United States Patent [19]
Luther

[11] Patent Number: 6,002,788
[45] Date of Patent: Dec. 14, 1999

[54] METHOD AND DEVICE FOR RENDERING CELLS OBSERVABLE WITH LASER SCANNING CYTOMETRY

[75] Inventor: Edgar A. Luther, Wilmington, Mass.

[73] Assignee: CompuCyte Corporation, Cambridge, Mass.

[21] Appl. No.: 08/937,038

[22] Filed: Sep. 24, 1997

[51] Int. Cl.⁶ .............................. G02B 21/08; G06K 9/28; G01N 21/00
[52] U.S. Cl. ............................................ 382/133; 356/338
[58] Field of Search .................................... 382/133, 134; 356/39, 337, 338, 129

[56] References Cited

U.S. PATENT DOCUMENTS 4,887,892  12/1989  Bacus ........................................ 382/133
5,369,037  11/1994  Hansen ....................................... 356/338

*Primary Examiner*—Amelia Au
*Assistant Examiner*—Samir Ahmed
*Attorney, Agent, or Firm*—Testa, Hurwitz & Thibeault, LLP

[57] ABSTRACT

A laser scanning cytometer, used with forward light scatter measurements, is provided with a laterally extended, asymmetrically positioned (relative to a light blocking position) light blocker, positioned between a cell sample and a detector such as a photodiode. The light blocker is asymmetrically positioned, at the reference position (i.e., no specimen) to permit some light to pass by a first end thereof and wherein light scatter caused by a specimen cell passes the first end, with other light scatter being blocked by the extended light blocker at a second end. Contrast of light scatter detection is sufficient thereby to provide viewable images of cells by means of the laser scanning cytometer.

4 Claims, 5 Drawing Sheets

METHOD AND DEVICE FOR RENDERING CELLS OBSERVABLE WITH LASER SCANNING CYTOMETRY

FIELD OF THE INVENTION

This invention relates to laser scanning cytometry measurements effected by forward light scatter and the imaging of actual cells thereby.

BACKGROUND OF THE INVENTION

Laser scanning cytometry is an effective diagnostic tool in determining various characteristics of cells including abnormalities, for the facilitated treatment of diseases and conditions associated with such abnormalities. It is not however designed for actual visual imaging of cell configuration and features. The construction and use of laser scanning cytometers has been described by Kamentsky and Kamentsky (Cytometry, 12:381–387, 1991) and in U.S. Pat. Nos. 4,647,531 and 5,072,382, the disclosures of which are incorporated herein by reference thereto.

In summary, a laser scanning cytometer such as the LSC™ cytometer, available from CompuCyte Corp., scans cell specimens, on a microscope slide positioned on a microscope stage, with a laser beam which is oscillating in the Y direction of the microscope stage. Voltage levels from optical detectors are synchronized and digitized to produce a raster of values from captured light. Subsequently, the microscope stage is advanced in the X direction, and the scan digitization is repeated. The cycle is repeated until a two dimensional (x-y) array of measurements is acquired. This two dimensional array is segmented by image processing techniques, and features for cells or objects of interest on the specimen are extracted and stored in a list mode data file.

One of the parameters measured by the LSC is forward light scatter. In this mode of operation, a focused laser beam passes through the specimen slide and laser scattered light is intercepted by a blocker bar before reaching a photodiode detector located beneath the blocker bar. In the reference position where there is no object in the laser beam path, the laser light is entirely prevented from reaching the detector, and the output of the detector is a low (zero) voltage signal. When a cell or other object is in the path of the laser beam, laser light is diverted from its original path, and is scattered over a range of angles (i.e., forward light scattering). A portion of this scattered laser light bypasses the blocker bar and strikes the face of the detector which provides an output signal characteristic of the particular way the light is blocked and scattered.

The output signal from the detector increases proportionally relative to the amount of light scatter. The resulting two dimensional memory array image appears as a dark field image with a black background, with the objects of interest appearing as a generally undefined bright image. There is however no physical image of the actual cells which can be discerned.

Laser scatter and absorption have been used extensively in flow cytometers and with other similar instruments, wherein data from either single or combined sensors are obtained as values for a cell in toto, with no capabilities for cellular imaging and subsequent localization of cellular constituents. Slit scan flow techniques extract subcellular information about cells, but still do not provide images of the cells.

SUMMARY OF THE INVENTION

It is accordingly an object of the present invention to provide a method and device which utilize laser scatter, negative scatter and light absorption to produce actual discernible images of cells with use of a diagnostic instrument such as a laser scanning cytometer.

It is a further object of the present invention to control the light striking a light detector (scattered from a specimen cell) in a cell diagnostic device, such as a laser scanning cytometer, by utilizing an asymmetrically positioned elongated blocker bar or disk or annulus, located between the specimen and the light detector and selectively blocking light and light scatter.

Generally the present invention comprises a method for cell imaging by use of a light emitting evaluation and diagnostic device such as a laser scanning cytometer, when used with forward light scatter for diagnostic measurements. The device is provided with a laterally extended, asymmetrically positioned (relative to a light blocking position) light blocker, positioned between a cell sample and a detector such as a photodiode. The light blocker is asymmetrically positioned, at the reference position (i.e., no specimen) to permit some light to pass by one end thereof and wherein light scatter with a specimen passes this end with other light scatter being blocked by the extended light blocker at a second end. Contrast of light scatter detection is sufficient thereby to permit discerning of actual view images of cells by means of a laser scanning cytometer.

The method of the present invention comprises using light scatter in a light scanning diagnostic device to provide a viewable image of a cell specimen which is light scanned by the device. In the device, light from a light source is substantially blocked, by blocking means, from being detected by a light detector in the absence of a cell specimen. In the presence of a cell specimen it scatters light, as a function of the nature of the specimen, which scattered light is not blocked and is detected by the light detector for providing selected information about the cell specimen. The method comprises the steps of:

a) positioning and configuring the light blocking means in the light scanning device between the light source and the light detector such that a portion of non-scattered light is permitted to be detected by the light detector; and b) positioning and configuring the light blocker to permit only a selected portion of the scattered light, resulting from contact of the light with a cell specimen, to be detected by the light detector;

whereby contrast between the detected light and scattered light is sufficient to provide a visual image of the cell specimen.

With utilization of the non-confocal design of the optics of a laser scanning cytometer, there is a minimization of the effects of variations of the sample in the Z (focal plane) direction. This allows cells to be automatically relocated and imaged over a wide portion of a microscope slide. In contrast, techniques using standard optics, and with similar resolving power objectives, require manual focusing for each relocated event, especially with higher power objectives.

These and other objects, features and advantages of the present invention will become more evident from the following discussion and drawings in which:

SHORT DESCRIPTION OF THE DRAWINGS

DETAILED DESCRIPTION OF THE INVENTION

In effecting the method of the present invention of cell imaging, the light blocker of the present invention is configured, positioned and sized to prevent light from passing by one end and striking the light detector and this includes any expected scatter light. The other end is aligned relative to the normal laser light beam being utilized, whereby a small amount of non-scattered light passes the end (i.e., without specimen cell scanning) and wherein scattered light from a specimen cell is allowed to specifically pass this end to strike the detector.

The output of the detector is at a high (reference) level. When a cell intercepts the laser beam, and depending on the geometry and optical properties of the cellular components, it will either scatter additional light onto the light detector resulting in an increase in the amount of signal from the detector, or it will scatter light away from the portion of the beam which is hitting the scatter detector (negative scatter), resulting in a lowering in the signal from the detector. The resulting two dimensional memory image appears as a bright field image, with the cells and other objects appearing as objects with bright highlights (above the reference level) and dark "shadows" (below the reference level). The direction and the angle of the shadows is determined by the amount of asymmetry in the blocker bar detector system.

A parallel occurrence is that laser light can be absorbed by components of cells, especially if they have been stained with chromatic dyes with the appropriate absorbance characteristics. The absorption by the chromatic dyes is especially evident in the nuclei of the superficial cells, which appear dark.

DETAILED DESCRIPTION OF THE DRAWINGS AND THE PREFERRED EMBODIMENT

Figure 1A:
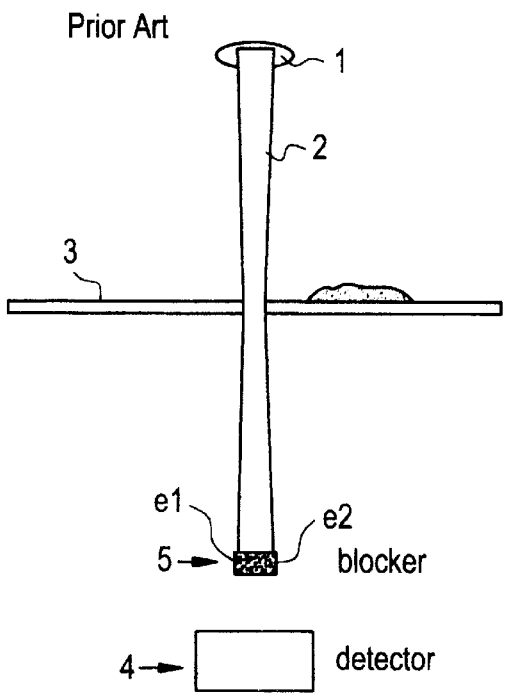
FIGS. 1a and 1b are schematic views of the optical detection and light scatter mode of a laser scanning cytometer in the "reference" and cell detecting modes respectively, of the prior art.
Figure 2A:
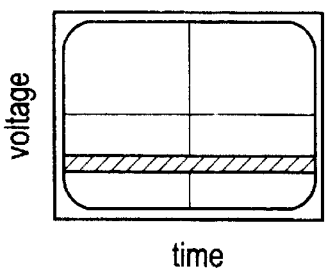
FIGS. 2a and 2b are graphs of voltage versus time for the detected light of the reference mode of FIG. 1a and of the cell detecting modes of FIG. 1b, respectively.

With specific reference to the drawings, in FIG. 1a, a schematic view of the optical detection system of a laser scanning cytometer is shown with laser light source 1 and beam 2 which beam passes through transparent slide 3 toward detector 4. Light blocker member 5 however prevents light from reaching the detector, in the reference mode shown in FIG. 1a. FIG. 2a is a resultant graph of voltage versus time as measured from the voltages determined by detector from incident light levels. The light level shown is low and indicative of no light passing the light blocker member 5 (i.e., full light blockage at the reference level or zero light level).

Figure 1B:
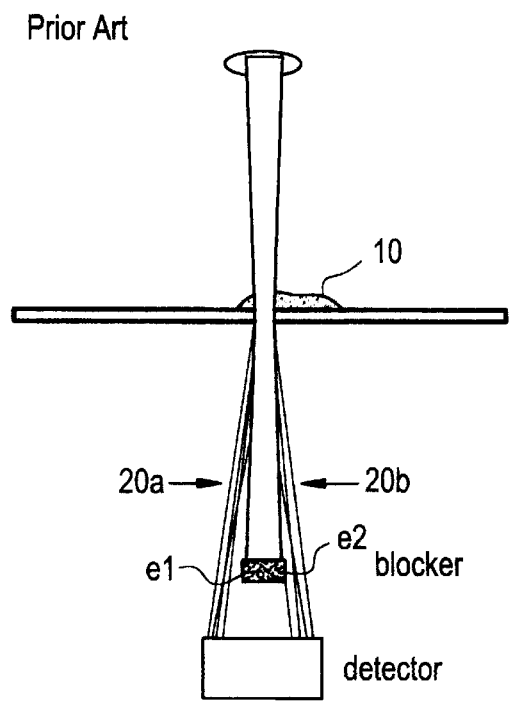
Figure 2B:
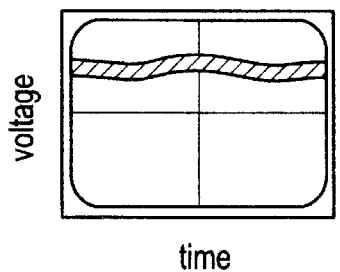
Figure 5A:
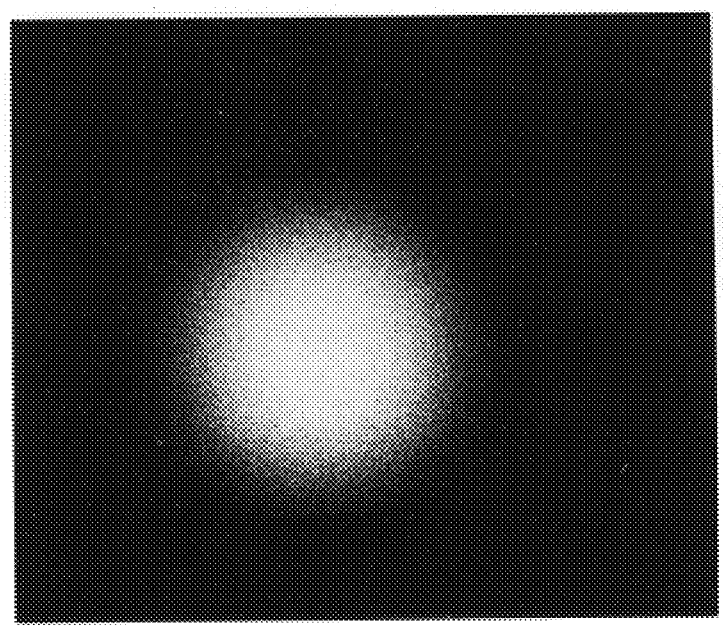
FIGS. 5a and 5b are photographs of the same detected and scanned cell as scanned in accordance with the prior art of FIG. 1b and the present invention in FIG. 3b, respectively.

In contrast, beam 2 is shown in FIG. 1b as striking cell specimen 10 with the light beam being scattered into elements 20a and 20b which pass the ends e1 and e2 of blocker member 5 to strike detector 4 thereby providing the light and dark contrast image shown in FIG. 5a. A graph of voltage versus time for the detected light scatter is shown in FIG. 2b with the higher detection voltage and therefore higher light levels.

Figure 3A:
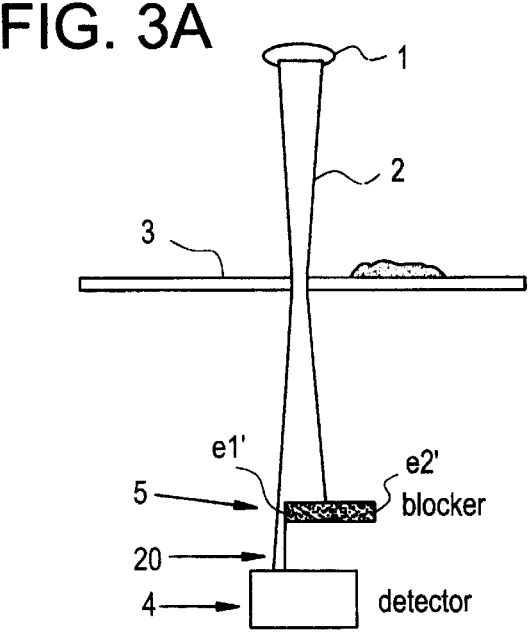
FIGS. 3a and 3b are the optical detection and light scatter modes of FIGS. 1a and 1b, modified in accordance with the present invention.
Figure 3B:
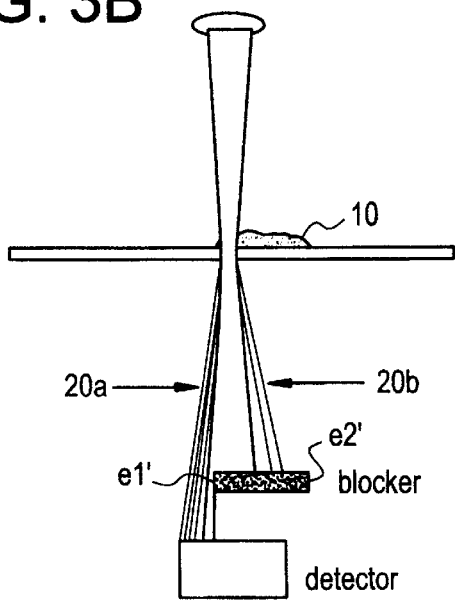
Figure 4A:
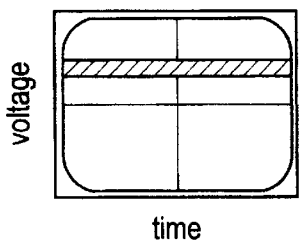
FIGS. 4a and 4b are graphs of voltage versus time for the detected light of the reference mode of FIG. 3a and of the cell detecting mode of FIG. 3b, respectively.
Figure 4B:
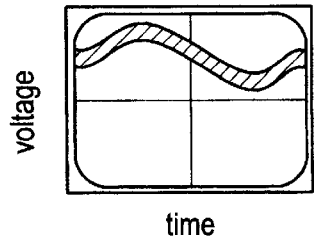
Figure 5B:
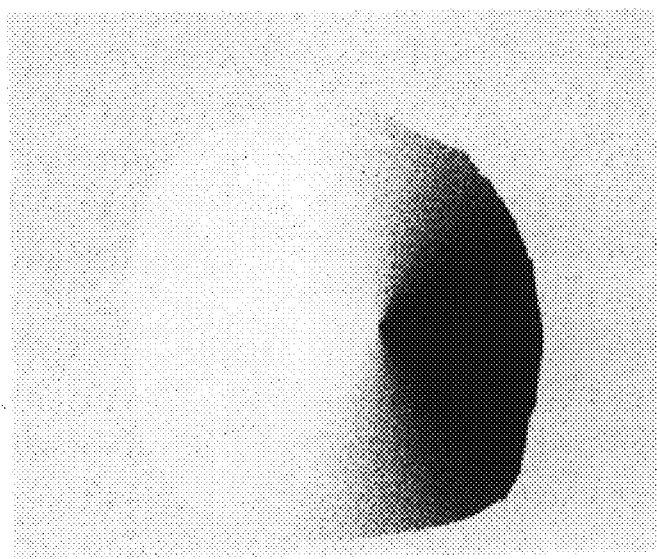

The same schematic optical system is shown in FIGS. 3a and 3b with light source 1 and beam 2, detector 4 and slide 3 with specimen 10 thereon. However in such Figures, light blocker 5 is modified as being elongated and asymmetrically positioned such that a portion 20 of the beam 2 passes end e1' of blocker 5 to strike the detector 4 even without light scatter. The graph in FIG. 4a illustrates the higher light level in the non-scatter reference mode. In FIG. 3b, cell specimen 10 is light scanned by beam 2 with resultant light scatter 20a and 20b. Light scatter 20a passes by end e1' of light blocker 5 to strike detector 4. However light scatter 20b is blocked by end e2' from striking the detector 4. The voltage v. time graph shown in FIG. 4b exhibits more pronounced voltage fluctuations which translates into the image shown in FIG. 5b wherein contrast levels are visible as an image of the cell specimen.

Figure 6:
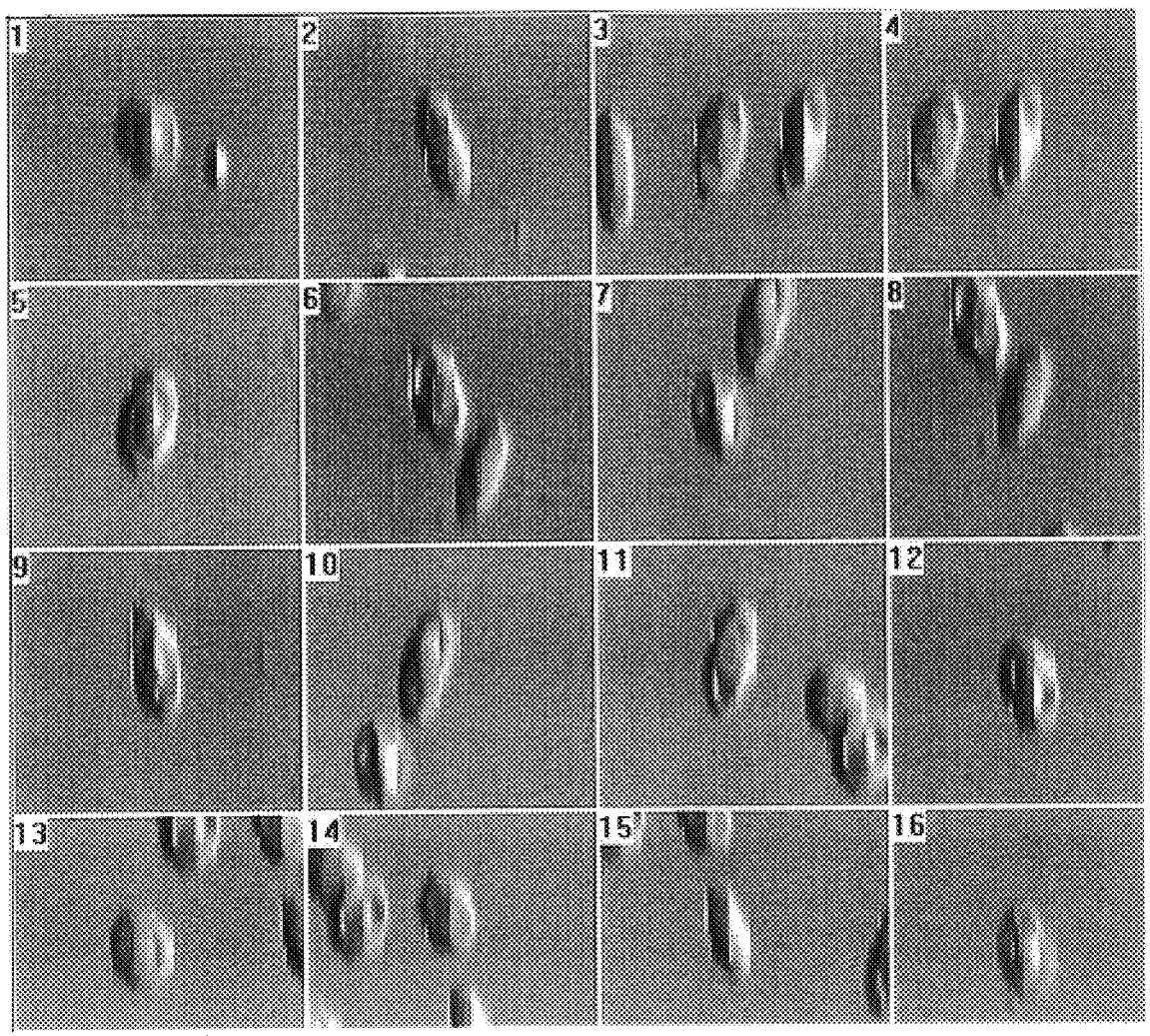
FIG. 6 is a photograph of a laser scatter image of CRBC as detected and scanned in accordance with the present invention.
Figure 7:
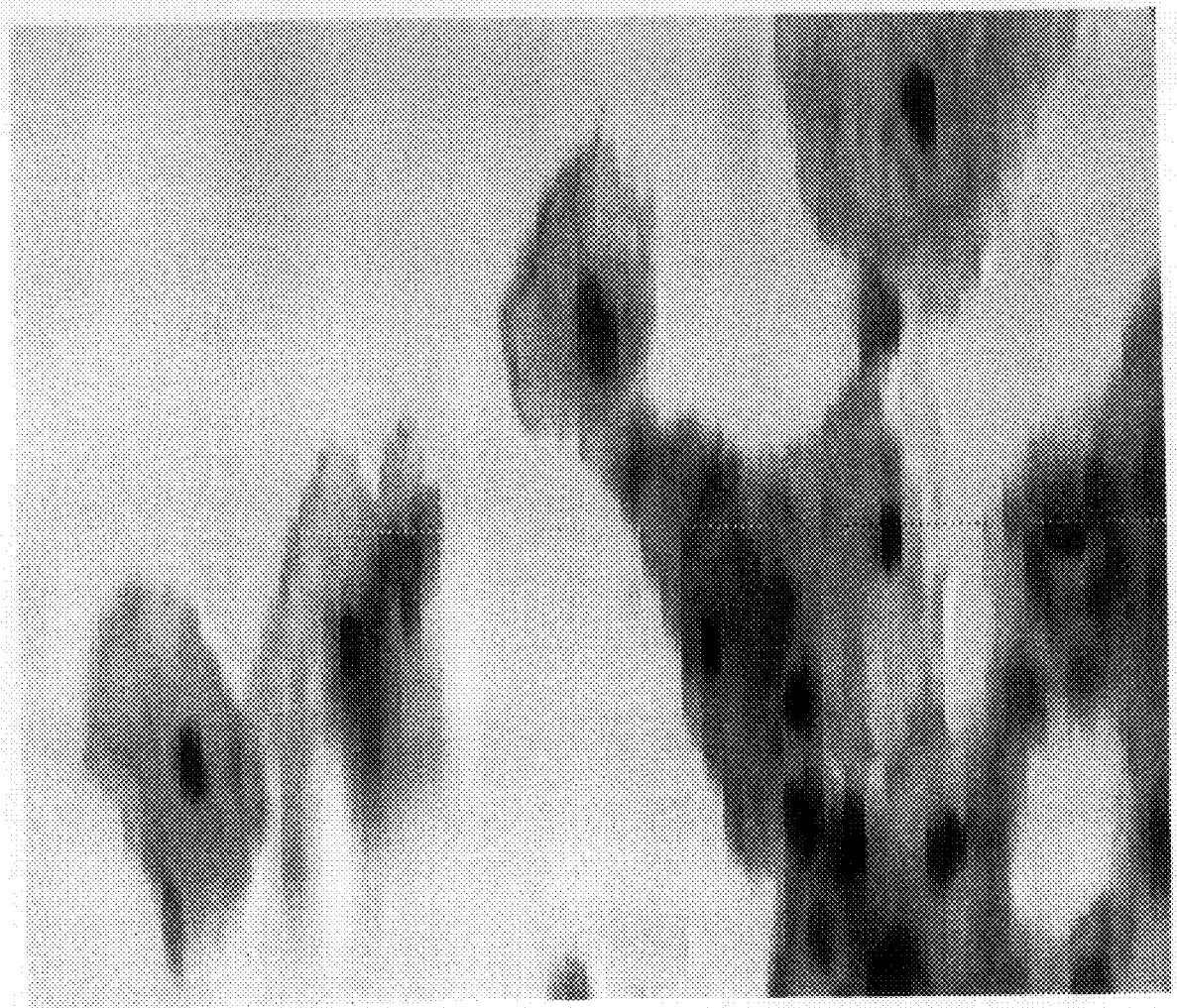
FIG. 7 is a photograph of a laser absorption image of a Pananicolou stained Cytyc Thinprep cell specimen.

By utilizing the optical system as modified as shown in FIGS. 3a and 3b, it is possible to obtain images of chicken erythrocytes as shown in the photograph of FIG. 6. In addition, components of cells may absorb laser light particularly if they have been stained with chromatic dyes of the appropriate absorbance characteristics. Memory images of scans measuring absorbance are bright field images, with dark areas representing the cells. This is seen in FIG. 7, which is a photograph of a laser scan image of a Papanicolou stained Cytyc Thinprep of a gynecological sample that was scanned with the modified light scatter configuration. The absorption by the chromatic dyes is especially evident in the nuclei of the superficial cells, which appear dark.

It is understood that the above description and examples are only illustrative of the present invention and that changes in structure and components of light emitting diagnostic devices and the method used is possible without departing from the scope of the present invention as defined in the following claims.

What is claimed is:

1. A method of using light scatter in a light scanning diagnostic device to provide a viewable image of a cell specimen which is light scanned by said device, wherein in said device, light from a light source is normally substantially blocked, by blocking means, from being detected by a light detector in the absence of a cell specimen and wherein a cell specimen scatters light, as a function of the nature of the specimen, which scattered light is not blocked and is detected by the light detector for providing selected information about the cell specimen, the method comprising the steps of:

a) positioning and configuring the light blocking means in the light scanning device between the light source and the light detector such that a portion of non-scattered light is permitted to be detected by the light detector and a portion of the non-scattered light is blocked from being detected by the light detector; and b) positioning and configuring the light blocker to permit only a selected portion of the scattered light, resulting from contact of the light with a cell specimen, to be detected by the light detector; wherein the light blocker is further positioned between the cell specimen and the light detector to block a different selected portion of the scattered light from being detected by the light detector;

whereby contrast between the detected light and scattered light is sufficient to provide a visual image of the cell specimen.

2. The method of claim 1, wherein the device is a laser scanning cytometer.

3. A light scanning diagnostic device, comprising a light source, a light detector and light blocking means, wherein the device provides a viewable image of a cell specimen which is light scanned by the device, wherein in said device, light from the light source is selectively blocked, by the light blocking means, from being detected by the light detector and wherein a cell specimen scatters light, as a function of the nature of the specimen, which scattered light is detected by the light detector for providing selected information about the cell specimen, characterized in that the light blocking means is positioned between the light source and the light detector such that a portion of non-scattered light is permitted to be detected by the light detector; and wherein the light blocking means is further positioned and configuring to permit only a selected portion of the scattered light, resulting from contact of the light with a cell specimen, to be detected by the light detector; whereby contrast between the detected non scattered light and scattered light is sufficient to provide a visual image of the cell specimen.

4. The device of claim 3, wherein the device comprises a laser scanning cytometer.

\* \* \* \* \*